(12) United States Patent
Forth

(10) Patent No.: US 8,356,533 B2
(45) Date of Patent: Jan. 22, 2013

(54) TATTOO GUN SPRING TENSIONER

(76) Inventor: Emerson Forth, Miami Beach, FL (US)

(*) Notice: Subject to any disclaimer, the term of this patent is extended or adjusted under 35 U.S.C. 154(b) by 372 days.

(21) Appl. No.: 12/644,354

(22) Filed: Dec. 22, 2009

(65) Prior Publication Data

US 2011/0146453 A1    Jun. 23, 2011

(51) Int. Cl.
*B43K 5/00* (2006.01)
(52) U.S. Cl. .......................................... 81/9.22; 81/438
(58) Field of Classification Search .................. 81/9.22, 81/438
See application file for complete search history.

(56) References Cited

U.S. PATENT DOCUMENTS

| | | | | |
|---|---|---|---|---|
| 4,159,659 A | * | 7/1979 | Nightingale | 81/9.22 |
| 6,282,987 B1 | * | 9/2001 | Moniz | 81/9.22 |
| 6,550,356 B1 | * | 4/2003 | Underwood | 81/9.22 |

* cited by examiner

*Primary Examiner* — Lee D Wilson
*Assistant Examiner* — Shantese McDonald
(74) *Attorney, Agent, or Firm* — Christopher J. Vandam, PA; Chris Vandam

(57) ABSTRACT

A tattoo gun improvement comprised of an adjustment means for the main spring of the tattoo gun that permits adjustment of the angle of the spring relative to the frame and therefore the spring tension against the needle depth adjuster. The means of adjustment facilitates quick and accurate tension setting on the spring while avoiding the need to bend the spring or alter the needle penetration setting adjustment. By avoiding bending the spring the spring life is extended as well as the precision that the spring tension may be adjusted. A precisely and properly adjusted spring can allow the tattoo gun to be used with less power that further can result in less unnecessary trauma to the skin.

1 Claim, 2 Drawing Sheets

TATTOO GUN SPRING TENSIONER

BACKGROUND OF THE INVENTION

1. Field of the Invention

The present invention relates to tattoo guns, and more particularly, to tattoo gun spring tensioning.

2. Description of the Related Art

Several designs for tattoo guns have been designed in the past. None of them, however, includes a means to selectively tune the tension on the spring without bending the spring itself and without affecting the depth of the needle stroke.

Applicant believes that the closest reference corresponds to U.S. Pat. No. 4,159,659 issued to Nightingale on Jul. 3, 1979. However, it differs from the present invention because the present invention allows a user to adjust the tension on the spring without bending the spring or affecting the depth of the needle stroke. Nightingale does have some adjustability but only on the rear spring and not on the front spring as is critical in the present invention.

The Nightingale device, as in all known prior art, requires adjusting the bend in the spring to adjust tension which leads to imprecise results and metal fatigue which results in the spring losing its tune and ultimately spring failure. The Nightingale device also does not permit precise, consistent and long lasting tuning to the spring whereas the present invention allows a user of the device to easily and consistently properly tune the tension on the spring.

Other patents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a tattoo gun that is easy to consistently tune the spring to a desired tension.

It is another important object of the present invention to provide a means to adjust the tattoo gun spring independently from the depth stop adjustment while also avoiding the need to bend the spring for adjustments.

It is another object of this invention to provide a device that retains the spring tension setting and improve the life span of the spring by avoiding metal fatigue failures by avoiding the necessity to bend the spring.

It is still another object of the present invention to provide a tattoo gun that can be operated on less power when the spring is properly tuned and not over-tuned thereby saving energy and increasing the safety of the device for the artist and the one receiving the tattoo.

It is an additional object of the device to allow a low tension tuning of the spring to be consistently achievable thereby allowing softer needle strokes which in turn reduce damage to the skin being tattooed and decreases healing time and less blood loss.

It is another object of the present invention to allow the tension on the spring to be adjusted without bending the spring to facilitate the device handling both shading needles and lining needles.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Tattooing skin has been practiced through millennia. Generally, a colorant or ink is placed onto the skin and a needle is used to pierce the epidermis and dermis allowing the colorant to penetrate the skin where it remains. A completed tattoo is formed from thousands of dots each from an individual pierce of the needle. Since the electrical age tattoo guns have been available that rapidly reciprocate a needle to aid in producing a tattoo.

In most tattoo guns used today a needle is affixed to a flat springy piece of metal known as a spring. An electromagnet draws the spring down and then releases it in rapid succession to create a reciprocating action of the needle. The needle is pressed against the skin to create shallow perforations allowing the colorant to penetrate the skin thereby permanently coloring the skin.

Careful control of the reciprocating action of the needle is preferred for the best control of the results obtained by the tattoo gun. How firmly the spring presses against the depth adjuster affects the performance of the device by changing the tension on the spring therefore affecting how much action and play there is in the spring and the connected needle. For tattooing operations such as drawing outlines, the preferred tension on the spring relative to the depth adjuster is different than when shading or filling procedures are performed.

Until now the means to adjust the tension of the spring onto the depth stop adjuster has been to bend the spring to varying degrees. Bending the spring is imprecise at best and time consuming. Bending the metal spring also imparts metal fatigue on the spring which can cause it to fail or change springy-ness after prolonged use.

The present device includes an additional adjustment means to precisely and predictably adjust the tension on the spring against the depth stop adjuster without repeatedly bending the spring. This results in a finely tuned spring that is more controlled, uses less energy, produces less skin damage and lasts longer than any other tattoo gun known or available today.

Figure 1:
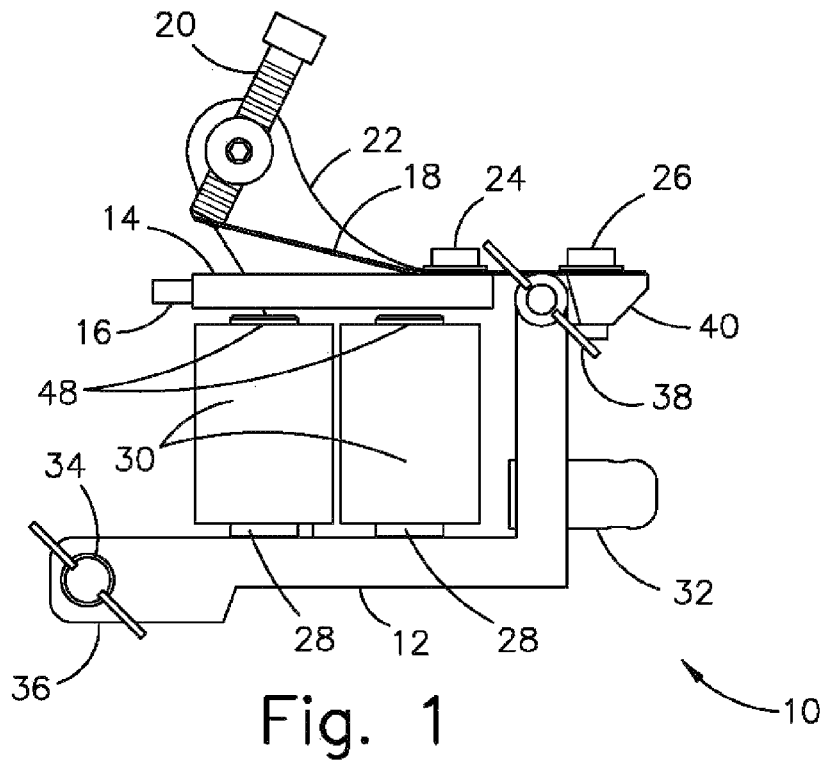
FIG. 1 represents an elevation view of the present invention.

Referring now to the drawings, where the present invention is generally referred to in FIG. 1 with numeral 10, it can be observed that it basically includes, inter alia, a frame 12, a bar 14, a point 16, a spring 18, an adjuster 20, an arm 22, a fastener 24, a fastener 26, spacers 28, electromagnets 30, a contact 32, fastener 34, guide 36, fastener 38, heel 40 and contacts 48.

When the device is in use a needle (not shown) is fixed onto the point 16 and fed through the guide 36. A needle tube (not shown) is often fit into guide 36 and held by fastener 34 to more accurately guide the needle and provide a means to hold the device. To reciprocate the needle an external power supply (not shown) rapidly cycles power on and off so that the electromagnets 30 turn on and off. When the electromagnets 30 are supplied power they attract bar 14 and pull against the spring 18 toward the contacts 48. The power is then momentarily interrupted and the spring 18 returns to its position up against the adjuster 20 taking point 16 and necessarily the needle with it. The electromagnet 30 on/off cycle is repeated hundreds of times per minute causing the needle to reciprocate up and down through the guide 36.

The frame 12 is generally provides the structure onto which the other elements of a tattoo gun are affixed. Integral to the frame 12 is the arm 22 that in the preferred embodiment of the device is immovable relative to the frame. The arm 22 supports the adjuster 20 that functions generally to adjust the stroke length that a tattoo needle (not depicted) has by limiting how far the bar 14 can move away from the electromagnets 30.

The primary moving parts of the invention are the spring 18 and bar 14. The spring 18 is affixed to the bar 14 by means of a fastener 24. Said spring 18 is connected to the heel 40 by means of fastener 26. Said fastener 24 or fastener 26 could be, for example, a screw, bolt or any other such means commonly available in the art to affix an object to another.

The heel 40 is adjustably connected to the frame 12 and secured relative to the frame 12 by means of fastener 38. Fastener 38 is preferably able to be tightened and loosened by hand such as by means of a wing nut. Because the spring 18 is connected to the heel 40 the spring 18 may be adjusted relative to the position of the frame 12 by loosening fastener 38 and rotating the heel 40 relative to the frame 12. Fastener 38 is then tightened to secure the angle of the spring 18 relative to the frame 12.

When no current is supplied to the device through contact 32 the spring 18 is biased away from the contacts 48 on the electromagnets 30 and the spring 18 is limited by the position of the adjuster 20. The circuit is completed by attaching a ground to anywhere on the frame other than the contact 32.

Spacers 28 electrically insulate the electromagnets 30 from the frame 12. Spacers 28 may optionally also provide a vibration dampening means if made of a pliable material such as a rubber so that when the bar 14 strikes the contacts 48 of the electromagnets 30 the impact force is absorbed by the spacers 28 and not transferred into the frame 12.

It is key to the performance of the device how much force is applied onto the adjuster 20 by the spring 18 when no current is supplied to the device. When the device is being prepared for use typically fastener 38 is loosened and the spring 18 is held against the adjuster 20 with appropriate force and then fastener 38 is re-tightened. Prior art designs such as that depicted in FIG. 2 require that spring 54 be bent against adjuster 64.

Figure 2:
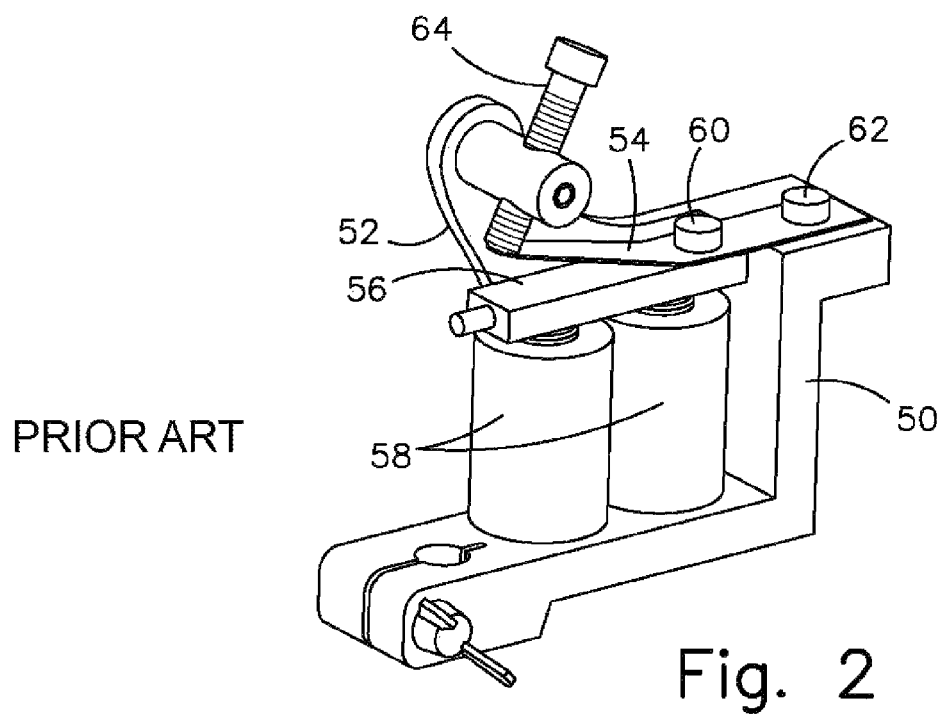
FIG. 2 shows a perspective view of the prior art.

FIG. 2 is an example of common tattoo guns in the prior art and is shown for comparative purposes to include, inter alia, a frame 50, an arm 52 a spring 54, a bar 56, electromagnets 58, fastener 60, fastener 62 and an adjuster 64.

The device in FIG. 2 operates in some ways similar to the present invention as generally shown in FIG. 1 in that said spring 54 is biased toward said adjuster 64 and when the electromagnets 58 are energized they attract bar 56. When the electromagnets 58 are not energized the spring 54 pulls the bar 56 away from the electromagnets 58. The cycle is repeated many times per minute and the needle reciprocates rapidly allowing the user to make many skin perforations in a shorter amount of time than otherwise possible.

A limitation with the prior art as shown in FIG. 2 results from the fixed geometry of the frame 50. The angle of the spring 54 relative to the frame 50 is permanently set when the frame 50 is forged. When the spring 54 is affixed to the frame 50 by means of fastener 62 the only way to change the relative angle is to bend the spring 54 which has inaccurate and inconsistent results which in turn reduces the accuracy of the device. The novel features of the present invention solves this inherent limitation in the prior state of the art.

Figure 3:
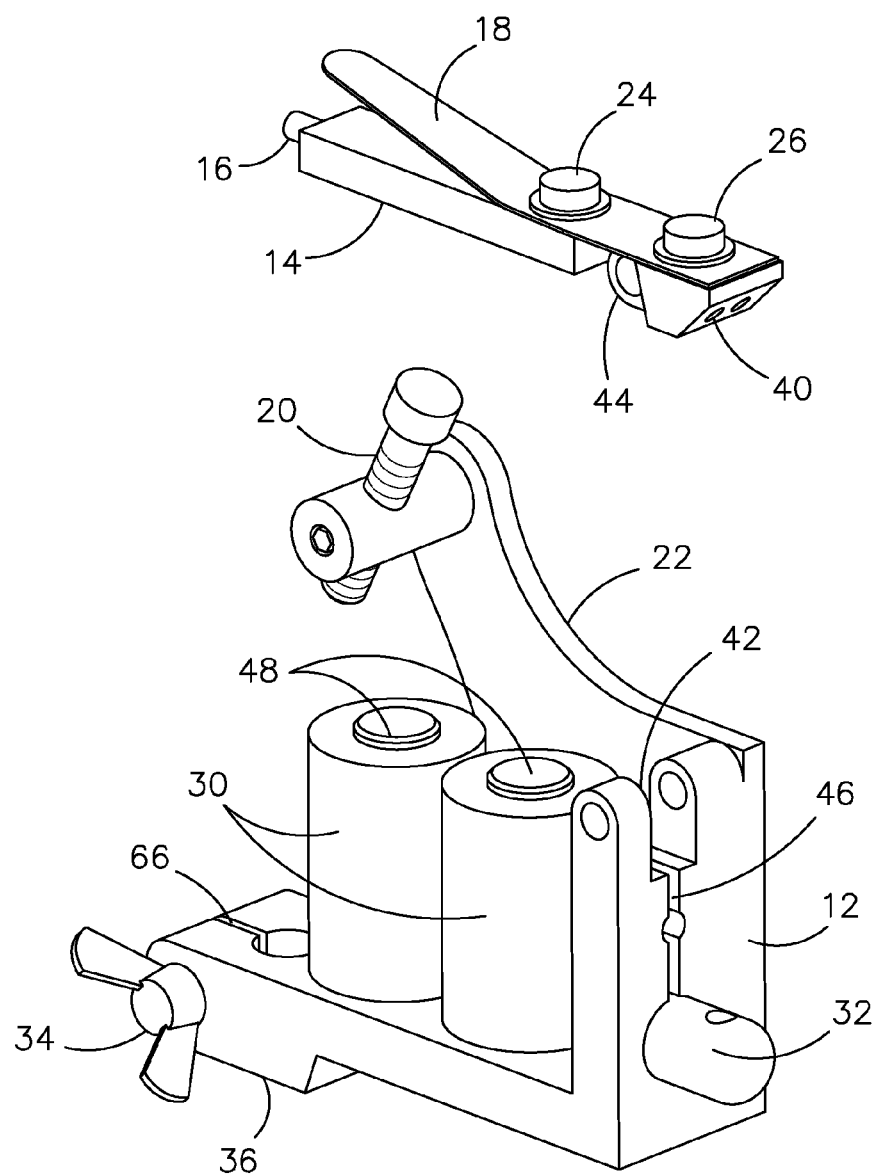
FIG. 3 illustrates an exploded perspective view of the present invention.

Now referring to FIG. 3 where the present invention is demonstrated in an exploded perspective view to provide more detail and further includes, inter alia, a yoke 42, an eye 44, a joint 46 and a joint 66. When the device is in use fastener 38 (shown in FIG. 1) passes through yoke 42 on the frame 12 and eye 44 on the heel 40. When the fastener 38 is tightened down the joint 46 compresses and the yoke 42 pinches the eye 44 thereby preventing any unwanted movement of the heel 40 relative to the frame 12.

To prepare the tattoo gun for use the user would typically loosen fastener 38 and rotate the spring 18 about the eye 44 and yoke 42 joint so that the spring 18 contacts adjuster 20. The tension on the spring 18 is set by holding the spring 18 against the adjuster 20 to the desired tension and then tightening the fastener 38. This is a much more precise and simple method than bending the spring 54 as would be required by the prior art shown in FIG. 2.

A similar joint 66 is also provided on the opposite end of the frame 12 that compresses under force applied by fastener 34 to hold a needle tube (not shown). The needle tube guides the needle and provides a safe and comfortable place to hold the tattoo gun while in use.

Arm 22 is shown more clearly in FIG. 3 where it can be seen to be integral to the frame 12. Arm 22, in the preferred embodiment, should not interfere with the movement of the heel 40 and spring 18 when adjusting the device. Arm 22 is contemplated to be further include a decorative design that does not contribute to the inventive functionality of the device. For example, an alternative to the goose neck design shown in FIG. 3 a lightning bolt or other non-functional design element could be included in the final design.

In a preferred embodiment of the invention is a tattoo gun comprising a frame having one or two electromagnets affixed thereto; a heel adjustably affixed to said frame; a spring affixed to said heel so that said spring is adjustable relative to said frame; said spring biased away from said electromagnets; said spring biased toward a depth adjuster; said spring disposed between said electromagnets and said depth adjuster. It can be further characterized in that a vibration dampening spacer is disposed between the electromagnetic coils and the frame. It can be further characterized in that said tattoo gun is battery powered.

Another embodiment of the invention is described as tattoo gun comprising a frame, a heel, a spring, an arm and a depth adjuster; said arm formed integral to said frame; said heel adjustably affixed to said frame; said spring affixed to said heel; said depth adjuster adjustably affixed to said arm; said spring biased toward said depth adjuster; where the strength of bias of said spring is adjustable by rotating said heel relative to said frame and where said heel is fixable relative to said frame; said spring being disposed between said depth adjuster and one or two electromagnetic means. It can be further characterized in that a vibration dampening spacer is disposed between the electromagnetic coils and the frame. It can be further characterized in that said tattoo gun is battery powered.

Another primary embodiment of the invention can be described as a direct current tattoo gun comprising one or two electromagnetic coils affixed to a frame; said frame having an arm terminating in an adjuster; a flat spring adjustably affixed on a first end to said frame; said flat spring being disposed between said electromagnetic coils and said adjuster; a magnetically attractable bar having a first end affixed to said spring and at a second end to a point suited for attachment to a tattoo needle; said spring biasing said bar away from said electromagnetic coils; said electromagnetic coils positioned to attract said bar; said spring being adjustable to impart more or less force onto said adjuster. It can be further characterized in that a vibration dampening spacer is disposed between the electromagnetic coils and the frame. It can be further characterized in that said tattoo gun is battery powered.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A tattoo gun comprised of a frame assembly and a spring assembly;
    said frame assembly is further comprised of a frame, a yoke, a fastener and an adjuster;
    said yoke is rigidly integral to said frame assembly;
    said spring assembly is further comprised of a bar, a spring and a heel;
    said bar has a first end and a second end and is magnetically attractive;
    said spring has a first end, a second end, a top surface and a bottom surface;
    said heel is rigidly affixed to said bottom surface of and at substantially the second end of said spring;
    said heel further includes an eye adapted to engage said yoke;
    said eye is articulatorily attached to said yoke so that said spring assembly may hinge relative to said frame assembly;
    said fastener has a first position that is adapted to fix said spring assembly relative to said frame assembly and has a second position that allows the separation between said spring assembly and said frame assembly;
    said spring has a bend at a predetermined point between said first end and said second of said spring;
    said bend is at a predetermined angle;
    said bar is affixed at its second end to said spring at a predetermined point on the bottom surface of said spring at a predetermined point between said heel and said bend;
    said bend in said spring biases the first end of said spring away from the first end of said bar.

* * * * *